United States Patent [19]
Greener

[11] Patent Number: 5,707,841
[45] Date of Patent: *Jan. 13, 1998

[54] PROCESS OF PRODUCING HIGHLY TRANSFORMABLE BACTERIAL CELLS AND CELLS PRODUCED THEREBY

[75] Inventor: Alan L. Greener, San Diego, Calif.

[73] Assignee: Stratagene, La Jolla, Calif.

[ * ] Notice: The term of this patent shall not extend beyond the expiration date of Pat. No. 5,512,468.

[21] Appl. No.: 637,003

[22] Filed: Apr. 18, 1996

Related U.S. Application Data

[63] Continuation of Ser. No. 151,577, Nov. 12, 1993, Pat. No. 5,512,468.
[51] Int. Cl.$^6$ .......................... C12N 15/64; C12N 1/20; C12N 1/21
[52] U.S. Cl. ................... 435/172.3; 435/252.33; 435/252.8
[58] Field of Search ............... 435/172.3, 252.8, 435/252.33, 320.1; 536/23.1

[56] References Cited

U.S. PATENT DOCUMENTS

| | | | |
|---|---|---|---|
| 4,493,893 | 1/1985 | Mielenz et al. | 435/172.3 |
| 5,512,468 | 4/1996 | Greener | 435/172.3 |

FOREIGN PATENT DOCUMENTS

| | | |
|---|---|---|
| 212 444 | 3/1987 | European Pat. Off. . |

OTHER PUBLICATIONS

Hanahan, D. 1983. J. Mol. Biol. vol. 166, pp. 557–580 "Studies on Transformation of *E. coli* with Plasmids".
Studier, F.W. 1991. J. Mol. Biol. vol. 219 pp.37–44. "Use of Bacteriophage T7 Lysozyme to Improve an Inducible T7 . . . ".

Cornelis et al., 1982, "Cloning and expression of a Bacillus coagulans amylase gene in Escherichia coli," *Mol. Gen. Genet.* 186(4):507–511.

Tsukagoshi et al., 1984, "Cloning and Expression of a Thermophilic α-Amylase Gene from *Bacillus stearothermophilus* in *Escherichia coli*," *Mol. Gen. Genet.* 193:58–63.

Antranikian et al., 1987, "Changes in the cell envelope structure of Clostridium sp. strain EM1 during massive production of alpha–amylase and pullulanase," *FEMS Microbiology Letters* 41:193–197.

Oriel and Schwacha, 1988, "Growth on starch and extracellular production of thermostable amylase by *Escherichia coli*," *Enzyme Microb. Technol.* 10:42–46.

*Primary Examiner*—Nancy Degen
*Attorney, Agent, or Firm*—Pennie & Edmonds LLP

[57] ABSTRACT

The invention provided herein includes gram negative bacteria cells containing a gene encoding an enzyme with carbohydrate degrading activity that had been rendered competent to transformation. Carbohydrate degrading enzymes of interest for use in the invention include alpha-amylase. The competent cells of the subject invention may be frozen so as to provide for prolonged storage. Other aspects of the invention include methods for rendering gram negative bacterial cells, such as *E. coli* cells competent to transformation. These methods involve the step of transferring a gene encoding an enzyme with carbohydrate degrading activity into *E. coli* cells and subsequently rendering the cells competent using any of a variety of competency inducing procedures.

13 Claims, No Drawings

PROCESS OF PRODUCING HIGHLY TRANSFORMABLE BACTERIAL CELLS AND CELLS PRODUCED THEREBY

This is a continuation of application Ser. No. 08/151,577, filed Nov. 12, 1993, now U.S. Pat. No. 5,512,468.

TECHNICAL FIELD OF THE INVENTION

The invention relates generally to the field of genetic engineering. More specifically, the invention relates to highly transformable bacterial cells and methods for producing such cells.

BACKGROUND OF THE INVENTION

A critical step in the in vitro formation of recombinant DNA constructs and the production of genetic libraries, as well as other genetic engineering techniques, is the process of inserting DNA (and other similar polynucleotides) into host cells. The process of introducing polynucleotides into host cells is referred to as transformation. Bacterial cells are frequently used as host cells for a wide variety of genetic engineering experiments. Among the most frequently used species of bacteria for genetic engineering experiments is the organism Escherichia coli (E. coli). E. coli does not naturally import exogenous DNA into the cell. E. coli must be subjected to a process that renders it amenable to uptake of exogenous DNA, i.e., a competency inducing procedure. E. coli, as well as other bacterial cells, that have been rendered capable of taking up exogenously added DNA are referred to as competent cells.

There are many established procedures for rendering E. coli cells competent. These procedures include the $CaCl_2$ incubation methods of Mandel and Higa, J. of Mol. Biol. 53:159 (1970), as well as numerous well-known variants thereof. Hanahan has made a detailed study of factors that effect the efficiency of transformation of E. coli cells (J. Mol. Biol. 166:557–580 (1983)) where he describes a method of producing highly competent E. coli cells comprising the step of washing E. coli cells in a buffer comprising potassium acetate, KCl, $MnCl_2$, $CaCl_2$, and hexamine cobalt chloride, which is generally regarded as the best available method of producing highly competent E. coli. Another method of producing competent E. coli cells is described by Jessee et al., U.S. Pat. No. 4,981,797. Jessee et al. shows that high levels of competency may be induced by growing E. coli cells in a temperature range of 18° C. to 32° C. as part of a competency inducing process.

The various techniques for rendering E. coli cells competent produce compositions of competent E. coli cells that vary widely in transformation efficiency. The mechanism by which DNA enters competent E. coli is not completely understood. Nor is it completely understood why one composition of competent E. coli cells differs in transformation efficiency from that of another composition of competent E. coli cells. Hanahan, in Escherichia Coli and Salmonella Typhimurium: Cellular and Molecular Biology, editor F. C. Neidhardt, American Society for Microbiology, Washington, D.C. (1987), provide a review of what is known about E. coli transformation. Only a fraction of the cells in a preparation of competent E. coli cells, i.e., a higher percentage of cells capable of being transformed, are necessarily competent for DNA uptake. Thus, some superior methods of generating competent E. coli cell compositions may simply result in the formation of competent cell compositions that contain a higher percentage of competent E. coli cells as opposed to containing E. coli cells that show individual levels of higher rates of DNA uptake or the ability to take up larger pieces of DNA. Alternatively, other methods of producing competent cells may result in the formation of competent E. coli cells that "individually" have higher transformation efficiencies. Hanahan, in J. Mol. Bio. 166:557–580 (1983) has speculated that competent E. coli cells contain channels for transport of DNA across the cell envelope and that the limiting step in determining the competency for transformation of E. coli cells are events that occur in the cell after the cell has taken up the DNA of interest, i.e., the establishment step. Another factor affecting the transformation efficiency of a composition of competent E. coli cells is the genotype of the cells. Some strains of E. coli are known to produce more highly transformable competent cell compositions than other strains of E. coli when subjected to the same competency inducing procedure. Hanahan, U.S. Pat. No. 4,851,348, describes how E. coli deoR mutants can be used to produce highly transformable E. coli cell compositions using a variety of competency inducing procedures.

Ever since it has been demonstrated that E. coli could be rendered competent to transformation, it has been of interest to produce the most competent E. coli cell preparations possible. The maximum level of transformation efficiency obtained using the method of Hanahan described in J. Mol. Bio. 166:557–580 (1987), which employs the step of washing cells in a buffer comprising potassium acetate, KCl, $MnCl_2$, $CaCl_2$, glycerol, and hexamine cobalt chloride, is approximately $1 \times 10^9$ transformants per microgram of supercoiled pUC18 plasmid DNA. On a per cell basis, this translates to approximately 1 cell out of 30 in the population actually becoming transformed. However, there continues to exist a need for new and improved methods for producing competent E. coli of superior transformability, as well as new strains of E. coli that demonstrate superior transformability. Such methods and strains would be of wide interest to most researchers in the field of genetic engineering in that the number of transformations required to obtain the desired result would be minimized. Thus, for example, larger genetic libraries could be built more easily as well as the construction of complex recombinant molecules achieved more readily.

SUMMARY OF THE INVENTION

The invention described herein provides a method of producing highly transformable gram negative bacterial cells such as E. coli that can be adapted to a wide variety of competency inducing procedures. The methods of the subject invention involve the introduction of genetic constructions containing a polynucleotide sequence encoding (and capable of expressing) an enzyme with carbohydrate degrading activity, preferably starch degrading activity. The enzyme is preferably located in the periplasmic space of the cell; however, the practice of the invention is not dependent upon any particular theory as to the cellular location of expressed carbohydrate degrading enzymes. Compositions of competent E. coli cells containing a genetic construction for the expression of an enzyme with carbohydrate degrading activity are shown to be more readily transformed with exogenous DNA than similar E. coli cells lacking such genetic constructions.

The invention provided herein includes E. coli cells containing a polynucleotide sequence encoding an enzyme with carbohydrate degrading activity that has been rendered competent to transformation. The carbohydrate degrading enzymes of interest include alpha-amylase, particularly alpha-amylase isolated from a thermophilic bacterium. The competent cells of the subject invention may be frozen so as to provide for prolonged storage.

Other aspects of the invention include methods for rendering gram negative bacteria, such as *E. coli* cells competent to transformation. These methods involve the step of transferring a polynucleotide sequence encoding an enzyme with carbohydrate degrading activity into *E. coli* cells and subsequently rendering the cells competent using any of a variety of competency inducing procedures, including the standard high competency induction method described in Hanahan *J. Mol. Bio.* 166:557–580 (1983) which comprises the step of washing the cells with a buffer comprising potassium acetate, $MnCl_2$, $CaCl_2$, glycerol, and hexamine cobalt chloride.

DESCRIPTION OF THE SPECIFIC EMBODIMENTS

The invention described herein includes gram negative bacteria, such as *E. coli* cells that have been genetically modified so as to exhibit increased transformation efficiency after being exposed to a competency inducing procedure in comparison with similar *E. coli* cells lacking the genetic construction. The cells of the subject invention have been modified by the addition of a genetic construction for the expression of a carbohydrate degrading enzyme, and preferably a starch degrading enzyme such as alpha-amylase. The addition of the genetic construction for the expression of a carbohydrate degrading enzyme to *E. coli* cells gives rise to *E. coli* cells that exhibit increased transformation efficiency after being rendered competent by a competency inducing procedure. The invention also includes compositions of competent *E. coli* cells containing a genetic construction for the expression of carbohydrate degrading enzymes, frozen compositions of such cells, and methods for making the competent cells.

The term carbohydrate-degrading enzyme as used herein refers to enzymes capable of hydrolyzing at least one type of linkage present between the constituent monosaccharide units of a carbohydrate molecule. The term "starch-degrading enzyme" as used herein refers to enzymes capable of hydrolyzing at least one type of linkage present between the constituent monosaccharide units of a starch molecule. The term "alpha-amylase" as used herein refers to enzymes capable of catalyzing hydrolysis of the $\alpha$-1$\rightarrow$4 glucosidic linkages of polysaccharides containing such glucosidic linkages such as starch or glycogen. Preferred carbohydrate degrading enzymes are starch degrading enzymes. Preferred starch degrading enzymes are alpha-amylases. Particularly preferred starch degrading enzymes for use in the invention are alpha-amylases isolated from thermophilic bacteria, especially the alpha-amylase gene from a recently isolated uncharaterized thermophilic bacterium. The polynucleotide sequence encoding this alpha-amylase from the uncharacterized thermophilic bacterium can be found on the FAMY plasmid present in the *E. coli* strains having the ATCC accession numbers 69480, 69481, and 69482.

Genetic constructions containing a polynucleotide sequence encoding a carbohydrate degrading enzyme for use in the subject invention are designed so as to provide for the expression of a carbohydrate degrading enzyme. The expression of the carbohydrate degrading enzyme may be either constitutive or inducible. Methods for expression of genes of interest in *E. coli* and other gram negative bacteria are well known. For examples of such techniques see *Gene Expression Technology: Methods and Enzymology*, Vol. 185, Goeddel, Editor, Academic Press, Incorporated, San Diego, Calif. (1991). The genetic construction containing the polynucleotide encoding the carbohydrate degrading enzyme of interest may be designed to either replicate autonomously in a bacterial cell or be incorporated into the genome of the bacterial cell. In addition to polynucleotide-sequence encoding a carbohydrate degrading enzyme, the genetic construction may comprise any one of a number of conventional genetic vectors such as plasmids, phages, phagemids, and the like. The genetic construction containing the polynucleotide encoding the carbohydrate degrading enzyme may be introduced into an *E. coli* cell by any of a variety of transformation techniques including transformation, conjugation, electroporation, and the like.

Competent *E. coli* cells of the subject invention are produced by subjecting *E. coli* cells containing a carbohydrate degrading enzyme encoding polynucleotide sequence for expression to a competency inducing procedure. The term "competency inducing procedure" refers to any procedure used to render *E. coli* cells competent to transformation by exogenous DNA. The term "transformation efficiency" is a measure of the competence level of a given composition of competent cells. Transformation efficiency is expressed in terms of the number of transformants obtained for each microgram (or other quantity) of exogenous DNA added to a competent cell composition. It will be appreciated by the person of ordinary skill in the art that the measured transformation efficiency of a given composition of competent cells using a given transformation protocol will vary in accordance with the particular exogenous DNA used in the transformation. Factors such as the size and topology of the exogenous DNA can affect the measured transformation efficiency. Competency inducing procedures for *E. coli* (and other gram negative bacteria) are well known to the person of average skill in the art of molecular biology. Although competency inducing techniques vary considerably from one another, almost all competency inducing techniques involve the exposure of the cell to multivalent cations and near 0° C. Competency inducing techniques for use in the subject invention include, but are not limited to, the $CaCl_2$ incubation method of Mandel and Higa (*J. Mol. Bio.*, 53:159 (1970)), the method of Hanahan, *J. Mol. Bio.*, 166:557–580 (1983) that employs the step of washing cells in a buffer comprising potassium acetate, KCl $MnCl_2$, $CaCl_2$, glycerol, and hexamine cobalt chloride. The method of Hanahan is particularly preferred for use in the subject invention. In addition to Hanahan *J. Mol. Bio.* 166:557–580 (1983), a detailed protocol for carrying out the standard high efficiency competency induction method, which employs the step of washing cells in a buffer comprising potassium acetate, KCl, $MnCl_2$, $CaCl_2$, glycerol, and hexamine cobalt chloride, can be found in, among other places, U.S. Pat. No. 4,981,797 (Jessee) and Sambrook et al., *Molecular Cloning: a Laboratory Manual*, 2nd Edition, Cold Spring Harbor Press (1989). Competent cells of the subject invention may be transformed using most well known transformation procedures, typically involving the step of exposing competent cells to a heat pulse in the presence of exogenous DNA. Examples of such transformation procedures can be found in Mandel and Higa, *J. of Mol. Biol.* 53:159 (1970) and Hanahan *J. Mol. Bio.* 166:557–580 (1983).

After the *E. coli* cells have been rendered competent by a competency inducing procedure, the cells may be frozen so as to retain their competence upon thawing. Frozen competent cells are a particularly useful embodiment of the invention because they may be stored for prolonged periods of time, thus avoiding the need to constantly produce fresh preparations of competent cells. Protocols for preparing frozen competent cells are known to the person of average skill in the art. An example of such a protocol can be found in Hanahan, *J. Mol. Bio.* 166:557–580 (1983).

The introduction of a genetic construction for the expression of a carbohydrate degrading enzyme into *E. coli* serves to increase the transformation efficiency of compositions of *E. coli* cells rendered competent for a wide variety of *E. coli* strains. The genotype of an *E. coli* cell strain containing a genetic construction for the expression of a carbohydrate degrading enzyme may be selected so as to be particularly useful for a given genetic engineering experiment. For example, cloning vectors that are screenable because of LacZα fragment complementation may contain a particular mutation within the LacZ gene. Similarly, the cell may contain various other deletions or mutations in order to provide for complementation by the transforming DNA. The host cell may either possess or lack a restriction-modification system in order to expedite cloning. The host cells may also lack one or more recombination systems, e.g., RecA, RecBC. Preferred *E. coli* strains for use in the invention are cells that contain a mutation in the deoR gene, as described in Hanahan, U.S. Pat. No. 4,851,348. Particularly preferred strains of *E. coli* for use in the invention are the XL1-Blue™ strain (Stratagene, La Jolla, Calif.), the XL1-Blue MR strain, and the SURE™ strain (Stratagene, La Jolla, Calif.) that have been modified by the addition of a genetic construction for the expression of alpha-amylase isolated from a thermophilic bacteria and have the ATCC accession numbers 69480, 69481 and 69482, respectively. The plasmid containing the alpha-amylase gene in the *E. coli* strains having ATCC accession numbers 69480, 69481 and 69482 may be readily transferred to other strains of bacteria using techniques well known to the person of average skill in the art. Similarly, the person of average skill in the art may excise the alpha amylase gene from plasmids in the *E. coli* strains having accession numbers 69480, 69481 and 69482 and transfer the alpha amylase gene to a new genetic construct prior to transferring the gene to a new strain of bacteria.

While reference is made to *E. coli*, other gram negative bacteria cells can be rendered more competent, for example, bacteria from the Genera *Pseudomonas, Rhizobium, Agrobacterium, Salmonella, Proteus, Shigella, Klebsiella* and the like.

The invention having been described above, may be better understood by reference to the following examples. These examples are offered for the purpose of illustrating the subject invention, and should not be interpreted as limiting the invention.

EXAMPLES

Example 1

CREATION AND TESTING OF HIGHLY COMPETENT E. COLI STRAINS

Background

An alpha-amylase gene from a recently isolated uncharacterized thermophilic bacterium was initially inserted onto an autonomously replicating plasmid DNA element, and then was introduced into several *E. coli* strains through conjugation. This alpha-amylase gene can be found in the *E. coli* strains having the ATCC accession numbers 69480, 69481, and 69482. The resultant alpha-amylase gene containing strains and the respective parent strain were rendered competent using the procedure of Hanahan (*J. Mol. Biol.* (1983)). The transformation efficiency of the alpha-amylase gene containing strains were compared with the transformation of similar strains lacking the alpha-amylase gene.

MATERIALS AND METHODS

The *E. coli* strains used in this work were the XL1-Blue, SURE™, XL1-MR, SCS-1, NM522, and BB4 strains. The genotype of these cells are as follows: SURE™ [e14$^-$ (mCrA), $\Delta$ (mcrCB - hsdSMR - mrr) 171, sbcC, recB, recJ, umuC::Tn5 (Kan$^r$), uvrC, supE44, lac, gyrA96, relA1, thi-1, endA1 [F' proAB, lacI$^Q$ Z$\Delta$M15, Tn10, (tet$^r$)]]; NM522 [supE, thi-1, $\Delta$ (lac-proAB), $\Delta$ (hsdSMR - mcrB)5 ($r_K$-$m_k$-), [F' proAB, lacI$^Q$ Z$\Delta$M15]]; XL1-Blue [recA1, endA1, gyrA96, thi-1, hsdR17, supE44, relA1, lac, [F'proAB, lacI$^Q$ Z$\Delta$ M15, Tn10 (tet$^r$)]]; XL1-Blue MRF' [$\Delta$ (mcrA) 183, $\Delta$(mcrCB—hsdSMR —mrr)173, endA1, supE44, thi-1, recA1, gyrA96, relA1, lac, [F'proAB, lacI$^Q$Z $\Delta$ M15, Tn10 (tet$^r$)]]; DH5α [supE44, $\Delta$ lac U169 ($\phi$80 lac Z $\Delta$ M15) hsdR17, recA1, endA1, gyrA96, thi-1, relA1]; SCS1: recA1, gyrA96, endA1, thi-1, hsdR17, supE44, relA1; BB4: e14$^-$ ($\Delta$mcrA), hsdR514, supE44, supF58, lacY1 or (lacIZY)$^6$, galK2, galT22, metB1, trpR55, $\Delta$ (argF-lac)u169, F'[lacI$^Q$Z$\Delta$M15 proABTn10(tet$^r$)]. The genotypes of these strains may also be found, among other places, in the appendix of the Stratagene (La Jolla, Calif.) 1993 catalog.

Transformation and competency inducing procedures were essentially by the standard high competency induction method described in Hanahan *J. Mol Bio.* 166:557–580 (1983).- Conjugal cell matings were carried out by mixing the donor and recipient cells of interest during their exponential growth phase at an equimolar ratio, incubating at 37° C. for 60 minutes with gentle agitation, and plating on the appropriate selection plates at $10^{-3}$ and $10^{-4}$ dilutions.

All DNA manipulations such as restriction enzyme digestion and ligation were performed using enzymes obtained from Stratagene (La Jolla, Calif.) following the recommended conditions of the manufacturer.

Cloning alpha-amylase gene onto RSF1010 derivative pAL205. pBM100, a pBluescript™ II vector derivative containing the amylase gene from a thermophilic bacterium was digested with XbaI and HindIII and the appropriate DNA fragment was isolated and ligated to pAL205 digested with these same two enzymes. The ligation mix was transformed into SCS 1 and Tet$^R$ Cam$^R$ colonies selected. Plasmid DNA from these transformants was isolated and subjected to restriction enzyme analysis to confirm the presence of the amylase gene.

Generation of FAMY by homologous recombination. *E. coli* strain BB4 (Rec$^+$, NalS, FlacI$^q$Z M15, proAB, Tn10 (tetR), was transformed with pAL205AMY DNA and Cam$^R$ colonies were selected. BB4 cells harboring pAL205AMY were then conjugally mated with XL1 MR cells (Nal$^R$, F, Tet$^S$, Cam$^S$) and Nal$^R$, Tet$^R$, Cam$^R$ exconjugants selected. Since pAL205AMY is not capable of self-transmissibility, the most likely means by which Cam$^R$ exconjugants could be obtained was by a homologous recombination event between the homologous Tet$^R$ genes on both plasmids in the BB4 (Rec$^+$) host prior to mating. The presence of the co-integrate plasmid was confirmed by mating this resultant strain, XL1-MRF AMY, with NM522(F'). All exconjugants from this "back" mating were simultaneously Tet$^R$ and Cam$^R$. In addition, PCR amplification of the XL1 MRF AMY using amylase specific primers yielded an amplification product that co-migrated on an agarose gel with a fragment amplified from pBM100 and pAL205AMY.

Transformation Protocol

The frozen competent cells produced by the method of Hanahan were thawed on ice. The cells were gently mixed by hand during thawing. 100 µl portions of the cells were placed into separated prechilled 15-ml Falcon 2059 polypropylene tube. 1.7 µl of β-mercaptoethanol was added (at a 1:10 dilution of stock 14.4M β-mercaptoethanol, diluted in high-quality water) to the 100 µl of bacteria, giving a final concentration of 25 mM. The contents of the tubes were swirled gently. The cells were then incubated on ice for 10 minutes with gentle swirling every 2 minutes. Either 10 or 100 µg of supercoiled pUC18 DNA was added to the cells with gentle swirling. The tubes were then incubated on ice for 30 minutes. The tubes were then subjected to a heat pulse in a 42° C. water bath for 30 seconds. The length of time of the heat pulse used here was important for maximizing transformation efficiency. The tubes were then incubated on ice for 2 minutes. 0.9 ml of preheated (42° C.) SOC medium was then added and allowed to incubate at 37° C. for 1 hour with shaking at 225–250 rpm. The transformation mixture was then transferred to plate containing the appropriate medium and antibiotics spread onto surface of the plate.

MEDIA AND SOLUTIONS

SOB Medium (per liter)
  20.0 g of tryptone
  5.0 g of yeast extract
  0.5 g of NaCl
  Autoclave
  Add 10 ml of 1M $MgCl_2$ and 10 ml of 1M $MgSO_4$/ liter of SOB medium prior to use
  Filter sterilize SOC Medium (per liter)
  SOB medium
  Add 1 ml of a 2M filter-sterilized glucose solution or 2 ml of 20% (w/v) glucose prior to use
  Filter sterilize NZY Modified Medium (per liter)
  5 g NaCl
  6 g $MgSO_4 \cdot 7H_2O$
  5 g yeast extract
  10 g N . Z amine
  Autoclave LB Plate Solution (per liter)
  10 g of tryptone
  5 g of yeast extract
  10 g of NaCl
  15 g of agar
  Autoclave TY Medium (per liter)
  8 g of tryptone
  5 g of NaCL
  5 g of yeast extract
  Adjust to pH 7.2–7.4 with NaOH
  Autoclave YT Top Agar (per liter)
  TY medium plus 6 g of agar
  Autoclave
  Cool to 55° C.
  Add sterile $MgSO_4 \cdot 7H_2O$ to a final concentration of 10 mM TY Plates (per liter)
  YT medium plus 15 g
  Autoclave
  Cool to 55° C.
  Add sterile $MgSO_4 \cdot 7 H_2O$ to a final concentration of 10 mM LB-Ampicillin Plates (per liter)
  Prepare the LB plate solution described above
  Cool to 55° C.
  Add ampicillin solution to a final concentration of 50 µg/ml (200 µg/ml) for TOPP 5 strain)
    50 mg of ampicillin
    10 ml of 1M $MgSO_4$ LB-Ampicillin-Methicillin Plate (per liter)
  Prepare LB plate solution described above
  Cool to 55° C.
  Add 20 µg of ampicillin and 80 µg of methicillin LB-Tetracycline Plates (per liter)
  Prepare the LB plate solution described above
  Cool to 55° C.
  Add tetracycline solution
    12–20 µg of tetracycline
    10 ml of water
    Store solution in a dark, cool place as this solution is light-sensitive while waiting of the LB plate solution to cool
  Cover plates with foil if left out at room temperature for extended time periods to protect the plates from light LB-Kanamycin Plates (per liter)
  Prepare the LB plate solution described above
  Cool to below 55° C.
  Add the kanamycin solution
    75 µg of kanamycin
    10 ml of 1M $MgSO_4$
  Store plates at 4° C.

RESULTS

Incorporation of the alpha-amylase gene into the genome of *E. coli* was accomplished by inserting the gene onto the F sex factor present in XL1-Blue, SURE, and XL1-Blue MRF strains. This method was superior to inserting the alpha-amylase gene onto the chromosome because the presence of the alpha-amylase gene on the F episome enabled the conjugal mating of the gene into any *E. coli* strain of interest. The alpha-amylase gene, initially cloned into pBluescript™ vector, was isolated by restriction enzyme digestion and re-cloned onto an RSF1010 plasmid (Bagdasarian et al, *Gene* 16:237–247 (1981)) derivative called pAL205. Plasmid pAL205 is identical to plasmid pAL400 described in Greener et al. Genetics 130:27–36 (1992), except for the following 2 modifications: (1) the luciferase gene has been replaced by the chloramphenicol resistance gene using HindIII and BglII restriction endonucleases, and (2) a promoter element from *Pseudomonas aeruginosa* has been cloned into the BamHI cloning site. This plasmid harbors a tetracycline resistance gene that is homologous to the tetracycline resistance gene carried on the F episome residing in XL1-Blue and SURE strains. Insertion of the amylase gene onto the F episome was accomplished in vivo, by homologous recombination between these two plasmids in *E. coli* strain BB4. This new episome, termed FAMY, was then conjugally mated into XL1-Blue, XL1-MR, and SURE™ strains to produce the ultra competent cell derivatives.

Transformation efficiencies for XL1-MR FAMY, SURE FAMY, XL1-MR, SURE, and DH5 alpha (purchased from GIBCO/BRL) were determined by standard procedures and are summarized in Table 1. The method of Hanahan (*J. Mo. Bio.* 166:557–580 (1983)) was used as the competency indices procedure. The data show that the FAMY derivatives of SL1-MRF and SURE had 4–5 fold greater transformation efficiency than standard XL1-Blue, SURE and DH5 alpha at equivalent DNA concentrations.

In order to determine that the other features present in the XL1-Blue FAMY and SURE FAMY were not perturbed, the cells were tested for infectibility by M13 phage (indicating presence of F), and phage lambda. The FAMY derivatives were identical to the original parent. In addition, plasmid minipreps (both by standard alkaline lysis and by Stratagene's Clear Cut™ miniprep system) have been performed successfully the miniprep yields appear no different than the parental strains. In addition, the miniprep DNA was sequenced and the results were excellent.

The relative transformation efficiency of the FAMY derivatives with ligated DNA as a substrate was tested. The results are shown in Table 2.

TABLE 1

COMPETENT CELL TRANSFORMATION EFFICIENCIES WITH SUPERCOILED DNA

| HOST | PICOGRAMS DNA | TRANSFORMANTS/ MICROGRAMS |
|---|---|---|
| XL1-Blue F AMY | 100 | $6.5 \pm 0.3 \times 10^9$ |
| XL1-Blue MRF AMY | 100 | $4.6 \pm 0.6 \times 10^9$ |
| SURE F AMY | 100 | $3.9 \pm 0.4 \times 10^9$ |
| XL1-Blue | 100 | $1.2 \times 10^9$ |
| SURE | 100 | $6 \times 10^8$ |
| DH5 alpha | 100 | $8.0 \times 10^8$ |

TABLE 1: Competent cells and transformation protocols were performed by the method of Hanahan, J. Mol. Bio. 166: 557–580 (1983). 100 or 10 picograms of supercoiled pUC18 DNA were added to 100 microliter aliquots of the cells and plated onto LB plates containing 100 micrograms/ml ampicillin.

TABLE 2

TRANSFORMATION EFFICIENCIES WITH LIGATED DNA

| HOST | | NUMBER OF TRANSFORMANTS |
|---|---|---|
| XL1-Blue | a | 26 |
| | b | 33 |
| XL1-Blue MRF AMY | a | 78 |
| | b | 97 |
| XL1-Blue F AMY | a | 130 |
| | b | 148 |

TABLE 2: Relative transformation efficiencies for XL1-Blue and the derivatives. The substrate DNA plasmid, 970-3, an 8.78 kb M13 derivative, was digested with EcoRI restriction endonuclease, and incubated overnight with T-4 ligase prior to transformation. The A and B refer to the esults obtained in two separate transformation experiments.

Example 2

TRANSFORMATION OF PULLANASE GENE CONTAINING STRAINS OF *E. COLI*

A DNA segment isolated from the hyperthermophilic bacterium ES1 encoding the starch-degrading enzyme pullalanase was cloned in to the Bluescript plasmid vector (Stratagene, La Jolla, Calif.). This plasmid was transformed into XL1-Blue cells (Stratagene, La Jolla, Calif.), which were then assayed by transformation with a chloramphenicol-resistant plasmid derivative of RSF1010 in order to determine whether expression of pullalanase at 37° C. increased the transformation efficiency of the cells. Preliminary results obtained under non-optimal conditions for the pullanase gene were inconclusive in demonstrating an reproducible improvement in transformation efficiency. However, it is possible that under different growth conditions, e.g., higher than 37° C. (since the pullalanase was derived from a hyperthermophilic organism), the transformation efficiency of the pullanase gene containing strain could be significantly higher than the control strain.

Biological Deposits

On Nov. 9, 1993, Applicants have deposited with the American Type Culture Collection, Rockville, Md., USA (ATCC) strains XL1-Blue FAMY (ATCC accession #69480), XL1-BLue MR FAMY (ATCC accession.#69481), and SURE™ FAMY (ATCC accession #69482). These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

Equivalents

All publications and patents mentioned in the above specification are herein incorporated by reference. The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

What is claimed is:

1. A method of preparing competent gram negative bacterial cells, said method comprising the steps of:
   transferring a vector comprising an alpha-amylase gene into gram negative bacterial cells, and
   treating the cells with a competency inducing procedure, whereby competent cells are produced.

2. The method of claim 1, wherein the alpha-amylase gene is isolated from a thermophilic bacterium.

3. The method according to claim 1, wherein the competency inducing procedure is a standard high competency induction procedure employing the step of washing the cells with a buffer comprising potassium acetate, KCl, $MnCl_2$, $CaCl_2$, glycerol, and hexamine cobalt chloride.

4. The method of claim 1, said method further comprising the step of freezing the competent cells.

5. A competent bacterial cell produced by the method of claim 4.

6. A competent bacterial cell produced by the method of claim 1.

7. The method of claim 1, wherein the bacterial cells are *E. coli*.

8. The method of claim 7 wherein the *E. coli* have a genotype selected from the group consisting of:
   (1) [e14⁻(mcrA), Δ (mcrCB-hsdSMR-mrr)171, SbcC, recB, recJ, umuC:: Tn5 (Kanʳ), UvrC, supE44, lac, gyrA96, relA1, thi-1, endA1 [F′ proAB, lacI<sup>q</sup> ZΔM15, Tn10, (tetʳ)]],
   (2) [recA1, endA1, gyrA96, thi-1, hsdR17, supE44, relA1, lac, [F′proAB, lacI<sup>q</sup> ZΔ M15, Tn10 (tetʳ)]], and
   (3) [Δ (mcrA) 183, Δ(mcrCB - hsdSMR - mrr) 173, endA1, supE44, thi-1, recA, gyrA96, relA1, Lac, [F′proAB, lacI<sup>q</sup>Z Δ M15, Tn10 (tetʳ)]].

9. A competent gram negative bacterial cell comprising a genetic construction for the expression of an alpha-amylase gene.

10. The competent bacterial cell according to claim 9, wherein the alpha-amylase gene is isolated from a thermophilic bacterium.

11. The competent bacterial cell according to claim 9, wherein the bacterial cell is *E. coli*.

12. The competent bacterial cell according to claim 11 wherein the *E. coli* has a genotype selected from the group consisting of:

(1) [e14⁻(mcrA), Δ (mcrCB-hsdSMR-mrr)171, SbcC, recB, recJ, umuC:: Tn5 (Kan$^r$), UvrC, supE44, lac, gyrA96, relA1, thi-1, endA1 [F′ proAB, lacI$^q$ ZΔM15, Tn10, (tet$^r$)]], (2) [recA1, endA1, gyrA96, thi-1, hsdR17, supE44, relA1, lac, [F′proAB, lacI$^q$ ZΔ M15, Tn10 (tet$^r$)]], and (3) [Δ (mcrA)183, Δ(mcrCB - hsdSMR - mrr)173, endA1, supE44, thi-1, recA, gyrA96, relA1, Lac, [F′proAB, lacI$^q$Z Δ M15, Tn10 (tet$^r$)]].

13. The competent bacterial cell according to claim 9, wherein the cell is frozen.

* * * * *